United States Patent [19]

Nakajima et al.

[11] Patent Number: 5,093,249

[45] Date of Patent: Mar. 3, 1992

[54] PROCESS FOR PRODUCTION OF DIHOMO-GAMMA-LINOLENIC ACID AND INHIBITOR FOR UNSATURATION REACTION AT DELTA5-POSITION OF FATTY ACID

[75] Inventors: Toshiaki Nakajima; Toshitsugu Shimauchi, all of Ciba, Japan

[73] Assignee: Idemitsu Petrochemical Co., Ltd., Tokyo, Japan

[21] Appl. No.: 524,647

[22] Filed: May 16, 1990

[30] Foreign Application Priority Data

May 24, 1989 [JP] Japan .................................. 1-128916
Jul. 18, 1989 [JP] Japan .................................. 1-183789

[51] Int. Cl.⁵ .......................... C12P 7/62; C12P 7/64
[52] U.S. Cl. ..................................... 435/135; 435/134
[58] Field of Search ............................ 435/135, 134

[56] References Cited

U.S. PATENT DOCUMENTS 4,916,066  4/1990  Akimoto ............................. 435/134

FOREIGN PATENT DOCUMENTS 0155420  9/1985  European Pat. Off. .
0252716  1/1989  European Pat. Off. .
0304049  2/1989  European Pat. Off. .

OTHER PUBLICATIONS

Shimizu et al., (1991) *Lipids, vol. 26* (7), 512–516, "Sesamin is a Potent and Specific Inhibitor of Δ5 Desaturase in Polyunsaturated Fatty Acid Biosynthesis".

S. Shimizu et al., "Production of Dihomo-gamma-linolenic Acid by Mortierella alpina is-4", 1989, pp. 237–241, Journal Of The American Oil Chemists' Society, vol. 66, No. 2.

*Primary Examiner*—Douglas W. Robinson
*Assistant Examiner*—Jon P. Weber
*Attorney, Agent, or Firm*—Frishauf, Holtz, Goodman & Woodward

[57] ABSTRACT

Dihomo-γ-linolenic acid is produced by cultivating a microorganism having an ability to produce dihomo-γ-linolenic acid on a culture medium containing a compound having an ability to inhibit an unsaturation reaction at a Δ5-position of fatty acid.

9 Claims, No Drawings

PROCESS FOR PRODUCTION OF DIHOMO-GAMMA-LINOLENIC ACID AND INHIBITOR FOR UNSATURATION REACTION AT DELTA5-POSITION OF FATTY ACID

BACKGROUND OF THE INVENTION

The present invention relates to a process for mass-production of dihomo-γ-linolenic acid (Δ8, 11, 14-eicosatrieneic acid) at low production costs by a fermentation method, and an inhibitor for an unsaturation reaction at a Δ5-position of fatty acid by microorganisms and animal cells.

For production of dihomo-γ-linolenic acid, there is known a method in which lipid containing dihomo-γ-linolenic is produced by adding sesame oil to a culture medium containing glucose as a main component and cultivating a microorganism belonging to the genus Mortierella (H. Yamada et al., J. Am. Oil Chem, Soc., Vol. 66, p. 237-241 (1989)).

As an inhibitor for an unsaturation reaction at a Δ5-position of fatty acid, sesamin or episesamin contained in sesame oil is known (H. Yamada et al., Nippon Nogei Kagakukaishi, Vol. 63, p. 676 (1989)). However, sesamin and episesamin are unsuitable for practical use, because their mass-production costs are high.

SUMMARY OF THE INVENTION

As a result of investigations on mass-production of dihomo-γ-linolenic acid by a fermentation method, it has been found that the object can be attained by adding a specified compound to a culture medium, and that the specified compound possesses an action to inhibit an unsaturation reaction at a Δ5-position of fatty acid.

The present invention relates to a process for producing dihomo-γ-linolenic acid which comprises cultivating a microorganism having an ability to produce dihomo-γ-linolenic acid on a culture medium containing a compound represented by the general formula:

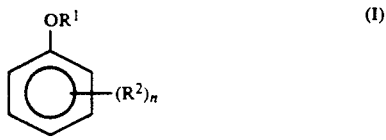

(wherein $R^1$ represents a lower alkyl group, $R^2$ represents a hydroxyl group, an alkyl group, an alkoxyl group, an alkenyl group, or an oxyalkyl group, and when there are a plurality of $R^2$s, they may be the same or different, and n represents an integer of 0 to 5), or curcumine, and recovering dihomo-γ-linolenic acid from the cultivated product.

The present invention further relates to an inhibitor for an unsaturation reaction at a Δ5-position of fatty acid, containing a compound represented by the above general formula (I), or curcumine as a main component.

DETAILED DESCRIPTION OF THE INVENTION

Any microorganisms can be used in the present invention as long as they have an ability to produce dihomo-γ-linolenic acid. For example, microorganisms having an ability to produce dihomo-γ-linolenic acid, belonging to the genus Conidiobolus of Mortierella can be used. Specific examples are *Conidiobolus nanodes* CBS 183/62, *Conidiobolus lamprauges* ATCC 12585, *Mortierella alpina* IFO 8568 and *Mortierella elongata* IFO 8570.

In the present invention, it is essential that the culture medium on which the above microorganisms is cultivated to produce dihomo-γ-linolenic acid contains a compound represented by the general formula:

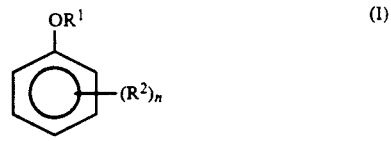

(wherein $R^1$, $R^2$ and n are the same as defined above), or curcumine.

In the above general formula, $R^1$, represents a lower alkyl group. The lower alkyl group includes a lower alkyl group having 1 to 6 carbon atoms, such as a methyl group, an ethyl group, a propyl group, etc. $R^2$ represents a hydroxyl group, an alkyl group, an alkoxyl group, an alkenyl group, or an oxyalkyl group. The alkyl group includes a methyl group, an ethyl group, a propyl group, a butyl group, a heptyl group, an octyl group, a nonyl group, etc (either straight-chain or branched). The alkoxy group includes a methoxy group, an ethoxy group, etc. The alkenyl group includes an allyl group, a 3-butenyl group, etc. The oxyalkyl group includes an oxymethyl group, a 2-oxyethyl group, a 3-oxypropyl group, a 4-oxybutyl group, etc. It is preferable that the alkenyl group, the alkoxyl group or the oxyalkyl group has a carbon atom or 2 to 6 carbon atoms. When there are a plurality of $R^2$s in the molecule, they may be the same or different. n represents an integer of 0 to 5.

Specific examples of the compounds represented by the above general formula (I) are anisole, dimethoxybenzene, diethoxybenzene, trimethoxybenzene, methoxytoluene, tertbutylhydroxyanisole (BHA), eugenol, etc. Many of the compounds are easily available because they are produced on a commercial scale as antioxidants for fats and oils, or perfume.

Curcumine is a main component of yellow dye contained in Ucon. Curcumine is easily available and furthermore its pure product can be obtained at low production costs. Ucon is used as a colorant for curry powder, pickled radish, pickled vegetables, and so on, and causes no problem in respect of safety. Although curcumine to be added to the culture medium may be either Ucon powder or fine curcumine product, the fine curcumine product is preferred in view of adverse influences of impurities, for example.

The amount of the compound of the general formula (I) or curcumine added is 0.01 to 10 g, preferably 0.05 to 2 g per liter of the culture medium. Addition of a greater amount of the compound of the general formula or curcumine is more preferred, as long as it does not inhibit the growth of microorganisms.

In connection with a method of adding the compound of the general formula (I) or curcumine, although the compound or curcumine can be added after dissolving in a suitable solvent such as ethanol, hexane, or dichloromethane, it is preferred that the compound or curcumine be added after mixing with lipid which is used as a carbon source of the culture medium. In connection with the time at which the compound of the general formula or curcumine is added, although it is preferred for the compound of the general formula (I)

or curcumine to be added before the start of cultivation, the compound or curcumine may be added at an intermediate point during the cultivation.

For cultivation of the above microorganisms, a culture medium containing a carbon source, a nitrogen source, inorganic salts, and so on is used. As the carbon source, carbohydrates or lipids, such as glucose, olive oil, sunflower oil, and γ-linolenic acid-containing oil can be used. The γ-linolenic acid-containing oil includes vegetable oil such as Evening primrose oil or Borage oil; and microorganism oil extracted from a fungus belonging to the genus Mortierella, Mucor or Cunninghamella. As the nitrogen source, an organic nitrogen source such as a yeast extract, pepton or a soybean cake is preferably used. As inorganic salts, potassium phosphate ($KH_2PO_4$), iron salt ($FeSO_4.7H_2O$), magnesium salt ($MgSO_4.7H_2O$), zinc salt ($ZnSO_4$), etc. are used. In addition, trace-elements or nutrient sources can be added, if necessary.

Cultivation of the above microorganisms is usually carried out by, for example, agitation cultivation or aeration cultivation, using a liquid medium. In connection with cultivation conditions, the cultivation temperature is 10° to 40° C. and preferably 20° to 32° C., and the cultivation time is 1 to 20 days. In the case of microorganisms belonging to the genus Conidiobolus, the cultivation time is preferably 3 to 10 days. In any case, the above conditions can be determined appropriately so as to increase the amount of dihomo-γ-linolenic acid produced, taking into consideration properties and so on of microorganism to be used.

In this way, dihomo-γ-linolenic acid is produced in the cultivated product. Thus this dihomo-γ-linolenic acid is recovered from the cultivated product. Although dihomo-γ-linolenic acid may be recovered as such from the cultivated product, it is preferred that microbial cells are separated from the cultivated product and dihomo-γ-linolenic acid is recovered from the cells, because the cultivated product contains lipids, for example, added as a carbon source. Recovery of dihomo-γ-linolenic acid is carried out by the usual technique such as solvent extraction or chromatography.

The inhibitor for the unsaturation reaction at the Δ5-position of fatty acid of the present invention will hereinafter be explained.

The unsaturation reaction at a Δ5-position as used herein refers to a conversion reaction of dihomo-γ-linolenic acid into arachidonic acid, for example.

The inhibitor for unsaturation reaction at Δ5-position of the present invention contains a compound represented by the general formula (I) or curcumine as a main component. The inhibitor is added to a mixture of a microorganism or animal cell and fatty acid in such a manner that the amount of the compound of the general formula (I) is 0.1 to 100 mg/g-dry cell and preferably 5 to 70 mg/g-dry cell, or the amount of curcumine is 0.01 to 100 mg/g-dry cell and preferably 0.1 to 20 mg/g-dry cell. The inhibitor of the present invention prevents the unsaturation reaction at the Δ5-position of fatty acid by the microorganism or animal cell.

In accordance with the present invention, dihomo-γ-linolenic acid can be produced with high efficiency, at low production costs, and in a large amount, because the arachidonic acid content in the microorganism or animal cell can be decreased and the dihomo-γ-linolenic acid content can be increased. Moreover, in accordance with the present invention, the unsaturation reaction at the Δ5-position of fatty acid can be prevented at low costs. Dihomo-γ-linolenic acid obtained is useful as a medicine or a biochemical reagent.

The present invention is described in greater detail with reference to the following examples.

COMPARATIVE EXAMPLE 1

To a culture medium having the composition shown in Table 1, 30 g/l of 16% γ-linolenic acid-containing oil (40% oleic acid, 10% linolic acid, 16% γ-linolenic acid) was added as a carbon source to prepare a culture medium. Then, 100 ml of the culture medium as prepared above was placed in a 500 ml Erlenmeyer flask and was sterilized at 121° C. for 15 minutes. *Conidiobolus nanodes* CBS 183/62 was inoculated to the flask and was subjected to cultivation at 30° C. for 4 days.

TABLE 1

| Composition of culture medium | |
|---|---|
| $KH_2PO_4$ | 3 g |
| $MgSO_4.7H_2O$ | 1 g |
| Pepton | 10 g |
| Yeast Extract | 5 g |
| $FeSO_4.7H_2O$ | 0.01 g |
| Distilled Water | 1 liter |

After the completion of cultivation, microbial cells were collected by centrifugal separation, washed with a phosphate buffer (pH 7.0), and then recovered by suction filtration. The microbial cells were placed in a stainless steel cup, and after addition of glass beads, methanol and chloroform, the microbial cells were crushed with a homogenizer and lipid in the microbial cells was extracted. The lipid thus extracted was subjected to methylesterification using $BF_3$-methanol, and its fatty acid composition was determined by gas chromatography. The results are shown in Table 2.

Identification of dihomo-γ-linolenic acid was carried out by the following method.

Authentic dihomo-γ-linolenic acid and a sample were mixed, and the resulting mixture was analyzed by capillary gas chromatography (column: PEG 20M). This analysis showed that a peak of a dihomo-γ-linolenic acid fraction was hightened. A triene fraction was separated from the sample by silver nitrate-impregnated thin layer chromatography. This fraction contained γ-linolenic acid and dihomo-γ-linolenic acid. From the triene fraction separated, dihomo-γ-linolenic acid was isolated by liquid chromatography (column: ODS). This dihomo-γ-linolenic acid was convered into a picolinyl derivative, and identified by a capillary gas mass spectrum. This confirmed that the sample was Δ8, 11, 14 eicosatrieneic acid, i.e., dihomo-γ-linolenic acid.

EXAMPLE 1

The same culture medium as in Comparative Example 1 was prepared, and a predetermined amount of tert-butyl-hydroxy anisol (BHA) as shown in Table 2 was added thereto. In more detail, a predetermined amount of BHA was dissolved in ethanol, and placed in a 500 ml flask. In addition, 3 g of 16% γ-linolenic acid-containing oil was added. The ethanol was evaporated in a stream of nitrogen, and BHA was mixed with the oil. Thereafter, 100 ml of the culture medium shown in Table 1 was added to prepare a culture medium. This culture medium was, after sterilization, inoculated with *Conidiobolus nanodes* CBS 183/62, and cultivation was carried out at 30° C. for 4 days. After the completion of cultivation, the fatty acid composition of lipid contained in the cells was analyzed by the same method as in Comparative Example 1. The results are shown in Table 2.

TABLE 2

|  | Comparative Example 1 | Example 1 | | |
|---|---|---|---|---|
| Amount of BHA (g/l) | 0 | 0.3 | 0.7 | 1.0 |
| Yield of Microbial Cells (g/l) | 22.0 | 24.4 | 21.0 | 17.4 |
| Yield of Lipids (g/l) | 6.8 | 7.7 | 6.5 | 6.0 |
| Composition of Fatty Acid (%) | | | | |
| Myristic acid ($C_{14:0}$) | 1.1 | — | 1.8 | — |
| Palmitic acid ($C_{16:0}$) | 24.1 | — | 26.1 | — |
| Stearic acid ($C_{18:0}$) | 4.1 | — | 4.6 | — |
| Oleic acid ($C_{18:1}$) | 27.0 | — | 30.0 | — |
| Linolic acid ($C_{18:2}$) | 6.1 | — | 6.7 | — |
| γ-Linolenic acid ($C_{18:3}$) | 6.3 | — | 6.3 | — |
| Eicosaenoic acid ($C_{20:1}$) | 3.0 | — | 1.9 | — |
| Dihomo-γ-linolenic acid ($C_{20:3}$) | 4.1 | 8.6 | 13.3 | 11.5 |
| Arachidonic acid ($C_{20:4}$) | 15.7 | 9.7 | 3.2 | 1.7 |
| Behenic acid ($C_{22:0}$) | 3.2 | — | 2.7 | — |
| Others | 5.3 | — | 3.4 | — |
| Yield of Dihomo-γ-linolenic acid (g/l) | 0.28 | 0.66 | 0.85 | 0.69 |

From the results of Table 2, it can be seen that addition of BHA markedly increases the dihomo-γ-linolenic acid content, leading to a relative decrease in the arachidonic acid content, and specifically inhibits the unsaturation reaction at the Δ5-position.

EXAMPLE 2

The procedure of Example 1 was repeated with the exception that a predetermined amount of compound and a predetermined cultivation time as shown in Table 3 were employed. The results are shown in Table 3.

TABLE 3

| Compound | (g/l) | Cultivation Period (days) | Yield of Microbial Cells (g/l) | Dihomo-γ-linolenic Acid Content (%) | Arachidonic Acid Content (%) | Yield of Dihomo-γ-linolenic Acid (g/l) |
|---|---|---|---|---|---|---|
| Anisole | 0.5 | 3 | 25.7 | 7.9 | 10.9 | 0.65 |
|  | 1.0 | 5 | 19.9 | 10.2 | 11.4 | 0.61 |
| o-Methoxyphenol | 0.5 | 4 | 20.4 | 10.9 | 7.8 | 0.67 |
| p-Dimethoxybenzene | 0.5 | 3 | 17.0 | 8.0 | 9.7 | 0.42 |
|  | 1.0 | 4 | 20.3 | 9.5 | 4.6 | 0.62 |
| Eugenol | 0.5 | 3 | 20.3 | 10.4 | 4.7 | 0.68 |
| BHA | 0.5 | 4 | 22.3 | 11.1 | 3.9 | 0.74 |
|  | 1.0 | 5 | 17.4 | 11.5 | 3.0 | 0.69 |
| 3-(4-Methoxyphenyl)propanol | 1.0 | 4 | 27.9 | 8.9 | 6.5 | 0.74 |
| m-Diethoxybenzene | 0.5 | 3 | 27.7 | 11.3 | 4.8 | 1.11 |
|  | 1.0 | 3 | 28.7 | 12.0 | 4.9 | 1.31 |
| p-Diethoxybenzene | 0.5 | 3 | 28.5 | 9.1 | 7.9 | 0.85 |
|  | 1.0 | 3 | 25.3 | 7.8 | 5.4 | 0.69 |
| 1,2,3-Trimethoxybenzene | 0.5 | 5 | 24.4 | 6.9 | 12.0 | 0.67 |
|  | 1.0 | 7 | 21.3 | 8.5 | 13.4 | 0.46 |
| 1,3,5-Trimethoxybenzene | 0.5 | 3 | 27.0 | 7.2 | 6.2 | 0.64 |
|  | 1.0 | 3 | 22.3 | 6.8 | 11.3 | 0.48 |
| p-Methoxytoluene | 0.5 | 4 | 34.8 | 10.8 | 11.6 | 1.19 |
|  | 1.0 | 4 | 40.8 | 10.0 | 7.8 | 1.10 |

EXAMPLE 3

To the culture medium shown in Table 1, but increased in concentration to three times the original one, 90 g/l of 16% γ-linolenic acid-containing oil was added, and further 2.1 g/l of BHA was added in the same manner as in Example 1 to prepare a culture medium. Then, 6 l of the culture medium was placed in a 10-liter jar fermentator, and then sterilized at 121° C. for 15 minutes. *Conidiobolus nanodes* CBS 183/62 which had been previously cultures on 600 ml of a culture medium prepared by adding 30 g/l of 6% γ-linolenic acid-containing oil to the culture medium shown in Table 1 was all inoculated to the above jar fermentator, and cultivation was carried out at 30° C. for days. After the completion of cultivation, the fatty acid composition of lipid contained in the microbial cells was analyzed by the same method as in Comparative Example 1.

The arachidonic acid content was 10%, the dihomo-γ-linolenic acid content was 15%, and the yield of dihomo-γ-linolenic acid was 3.3 g per liter of the culture medium.

EXAMPLE 4

The procedure of Example 2 was repeated with the exception that the amount of BHA added was changed to 1 g/l, and the microorganism inoculated was changed to *Conidiobolus lamprauges* ATCC 12585 and cultivation days were 4 days.

The yield of the microbial cells was 18.7 g/l, the yield of lipids was 5.8 g/l, the dihomo-γ-linolenic acid content was 9.3%, the yield of dihomo-γ-linolenic acid was 0.54 g/l, and the arachidonic acid content was 9.0%.

EXAMPLE 5, AND COMPARATIVE EXAMPLE 2

To the culture medium shown in Table 1, 30 g/l of 16% γ-linolenic acid-containing oil was added to prepare a culture medium of Comparative Example 2. To the culture medium shown in Table 1, 30 g/l of 16% γ-linolenic acid-containing oil and 0.5 g/l of BHA were added to prepare a culture medium of Example 5. These culture media were inoculated with *Mortierella alpina* IFO 8568, and cultivation was carried out at 20° C. for a predetermined period of time (days) shown in Table 4. After the completion of cultivation, the fatty acid composition of lipid contained in the microbial cells was analyzed by the same method as in Comparative Example 1. The results are shown in Table 4.

TABLE 4

|  | Cultivation Time (days) | Yield of Microbial Cells (g/l) | Dihomo-γ-linolenic Acid Content (%) | Arachidonic Acid Content (%) |
|---|---|---|---|---|
| Example 5 | 20 | 15.4 | 1.3 | 0.8 |
| Comparative Example 2 | 15 | 18.7 | 0.4 | 1.1 |

As apparent from Table 4, even when a microorganism belonging to the genus Mortierella is used, lipids in which the dihomo-γ-linolenic acid content is higher than the arachidonic acid content can be obtained.

EXAMPLE 6

The same culture medium as in Comparative Example 1 was prepared, and a predetermined amount of curcumine as shown in Table 5 was added thereto. In more detail, a predetermined amount of curcumine was dissolved in ethanol and then placed in a 500 ml flask. In addition, 3 g of 6% γ-linolenic acid-containing oil was added. In a stream of nitrogen, ethanol was evaporated, and curcumine was mixed with the oil. Thereafter, 100 ml of the culture medium shown in Table 1 was added to prepare a culture medium. After sterilization of the culture medium, *Conidiobolus nanodes* CBS 183/62 was inoculated and was subjected to cultivation at 30° C. for 4 days. After the completion of cultivation, the fatty acid composition of lipid in the microbial cell was analyzed by the same method as in Comparative Example 1. The results are shown in Table 5.

dium of Example 7. After sterilization at 121° C. for 15 minutes, the above culture media were inoculated with *Conidiobolus nanodes* CBS 183/62, and cultivation was carried out at 30° C. for 4 days. After the completion of cultivation, the fatty acid composition of lipid contained in the cells was analyzed by the same method as in Comparative Example 1. The results are shown in Table 6.

TABLE 6

| | Yield of Microbial Cell (g/l) | Yield of Lipids (g/l) | Dihomo-γ-Linolenic Acid Content (%) | Yield of Dihomo-γ-linolenic Acid (g/l) | Arachidonic Acid Content (%) | Yield of Arachidonic Acid (g/l) |
|---|---|---|---|---|---|---|
| Comparative Example 3 | 17.1 | 5.5 | 3.8 | 0.21 | 31.1 | 1.70 |
| Example 7 | 13.8 | 5.6 | 8.9 | 0.46 | 26.8 | 1.49 |

TABLE 5

| | Comparative Example 1 | Example 6 | | | |
|---|---|---|---|---|---|
| Amount of Curcumine (g/l) | 0 | 0.2 | 0.3 | 0.5 | 0.7 |
| Yield of Microbial Cells (g/l) | 22.0 | 27.0 | 30.6 | 27.9 | 16.4 |
| Yield of Lipids (g/l) | 6.8 | 8.3 | 11.2 | 8.5 | 5.1 |
| Composition of Fatty Acid (%) | | | | | |
| Myristic acid ($C_{14:0}$) | 1.1 | — | 0.9 | — | — |
| Palmitic acid ($C_{16:0}$) | 24.1 | — | 24.6 | — | — |
| Stearic acid ($C_{18:0}$) | 4.1 | — | 3.2 | — | — |
| Oleic acid ($C_{18:1}$) | 27.0 | — | 26.3 | — | — |
| Linolic acid ($C_{18:2}$) | 6.1 | — | 5.7 | — | — |
| γ-Linolenic acid ($C_{18:3}$) | 6.3 | — | 4.0 | — | — |
| Eicosaenoic acid ($C_{20:1}$) | 3.0 | — | 4.3 | — | — |
| Dihomo-γ-linolenic acid ($C_{20:3}$) | 4.1 | 8.2 | 15.7 | 16.1 | 14.0 |
| Arachidonic acid ($C_{20:4}$) | 15.7 | 8.9 | 9.6 | 4.2 | 4.6 |
| Behenic acid ($C_{22:0}$) | 3.2 | — | 3.3 | — | — |
| Others | 5.3 | — | 2.4 | — | — |
| Yield of Dimono-γ-linolenic acid (g/l) | 0.28 | 0.54 | 1.76 | 1.37 | 0.72 |

It can be seen from Table 5 that addition of curcumine markedly increases the dihomo-γ-linolenic acid content, leading to a relative decrease in the arachidonic acid content, and specifically inhibits the unsaturation reaction at the Δ5-position.

EXAMPLE 7, AND COMPARATIVE EXAMPLE 3

To the culture medium shown in Table 1, 10 g/l of glucose and 20 g/l of 16% γ-linolenic acid-containing oil were added to prepare a culture medium of Comparative Example 3. To the culture medium of Comparative Example 3, 0.3 g/l of curcumine was added in the same manner as in Example 6 to prepare a culture me-

EXAMPLE 8

To the culture medium shown in Table 1, but increased in concentration to three times the original one, 90 g/l of 16% γ-linolenic acid-containing oil was added, and further 0.5 g/l of curcumine was added by the same method as in Example 6 to prepare a culture medium. Then, 6 l of the culture medium prepared above was placed in a 10 l jar fermentator, and sterilized at 121° C. for 15 minutes. *Conidiobolus nanodes* CBS 183/62 which had been cultivated on 600 ml of a culture medium prepared by adding 30 g/l of 16% γ-linolenic acid-containing oil to the culture medium shown in Table 1 was all inoculated in the above jar fermentator, and cultivation was carried out at 30° C. for 4 days. After the completion of cultivation, the fatty acid composition of lipid contained in the cells was analyzed by the same method as in Comparative Example 1.

The arachidonic acid content was 10%, the dihomo-γ-linolenic acid content was 15%, and the yield of dihomo-γ-linolenic acid was 3.3 g/l.

EXAMPLE 9

The procedure of Example 6 was repeated with the exception that the amount of curcumine added was changed to 0.7 g/l, and the microorganism inoculated was changed to *Conidiobolus lampranges* ATCC 12585.

The yield of microbial cells was 20.3 g/l, the yield of lipids was 6.0 g/l, the dihomo-γ-linolenic acid content was 9.0%, the yield of dihomo-γ-linolenic acid was 0.54 g/l, and the arachidonic acid content was 8.8%.

EXAMPLES 10 TO 11, AND COMPARATIVE EXAMPLES 4 TO 5

To the culture medium shown in Table 1, 30 g/l of 16% γ-linolenic acid-containing oil was added to prepare a culture medium of Comparative Example 4 or 5. To the culture medium shown in Table 1, 30 g/l or 16% γ-linolenic acid-containing oil and 0.5 g/l of curcumine were added to prepare a culture medium of Example 10 or 11. These culture media were inoculated with *Mortierella alpina* IFO 8568 or *Mortierella elongata* IFO 8570, and cultivation was carried out at 20° C. for the predetermined period of time shown in Table 4. After the completion of cultivation, the fatty acid composition of lipid contained in the cells was analyzed by the same method as in Comparative Example 1. The results are shown in Table 7.

TABLE 7

| | Microorganism | Cultivation Period (days) | Yield of Microbial Cells (g/l) | Dihomo-γ-linolenic Acid Content (%) | Arachidonic Acid Content (%) |
|---|---|---|---|---|---|
| Comparative Example 4 | Mortierella alpina IFO 8568 | 15 | 18.7 | 0.4 | 1.1 |
| Example 10 | Mortierella alpina IFO 8568 | 15 | 13.2 | 1.9 | 1.3 |
| Comparative Example 5 | Mortierella elongata IFO 8570 | 10 | 17.3 | 0.8 | 2.3 |
| Example 11 | Mortierella elongata IFO 8570 | 10 | 14.1 | 1.8 | 0.2 |

It can be seen from Table 7 that even when a microorganism belonging to the genus Mortierella is used, there can be obtained lipids in which the dihomo-γ-linolenic acid content is higher than the arachidonic acid content.

What is claimed is:

1. A process for producing dihomo-γ-linolenic acid which comprises cultivating a microorganism having an ability to produce dihomo-γ-linolenic acid on a culture medium, said microorganism being a fungus selected from the group consisting of *Conidiobolus nanodes* CBS 183/62 and *Conidiobolus lamprauges* (ATCC 12585), said culture medium containing an effective amount of a compound selected from the group consisting of diethoxybenzene, methoxyphenol, tert-butylhydroxyanisole and eugenol and then recovering dihomo-γ-linolenic acid from the resultant cultivated product.

2. The process according to claim 1, wherein the amount of the compound added to the culture medium is 0.01 to 10 groups per liter of the culture medium.

3. The process according to claim 1, wherein the amount of said compound added to the culture medium is 0.05 to 2 grams per liter of the culture medium.

4. The process according to claim 2, wherein the cultivation is carried out at a temperature of 10° to 40° C. for 1 to 20 days.

5. The process according to claim 3, wherein the cultivation is carried out at a temperature of 20° to 32° C. for 3 to 10 days and the microorganism is *Conidiobolus nanodes* CBS 183/62.

6. The process according to claim 4, wherein the culture medium contains a carbon source selected from the group consisting of glucose, olive oil, sunflower oil, Evening primrose oil, Borage oil, an oil extracted from a fungus belonging to the genus Mortierella, an oil extracted from a fungus belonging to the genus Mucor and an oil extracted from a fungus belonging to the genus Cunninghamella; a nitrogen source selected from the group consisting of yeast extract, pepton and soybean coke; and an inorganic salt selected from the group consisting of $KH_2PO_4$, $FeSO_4.7H_2O$, $MgSO_4.7H_2O$ and $ZnSO_4$.

7. The process according to claim 5, wherein said compound is tert-butyl-hydroxyanisole in an amount of 0.3 to 1.0 grams per liter of the culture broth.

8. The process according to claim 5, wherein the amount of said compound is 0.5 to 1.0 grams per liter of the culture broth.

9. The process according to claim 4, wherein the microorganism is *Conidiobolus lamprauges* ATCC 12585; said compound is tert-butyl-hydroxyanisole in an amount of 1 gram per liter of the culture broth and the cultivation is carried out for 4 days.

* * * * *